(12) United States Patent
Rivin

(10) Patent No.: US 7,235,103 B2
(45) Date of Patent: Jun. 26, 2007

(54) ARTIFICIAL INTERVERTEBRAL DISC

(76) Inventor: Evgeny I. Rivin, 4227 Foxpointe Dr., West Bloomfield, MI (US) 48323

( * ) Notice: Subject to any disclaimer, the term of this patent is extended or adjusted under 35 U.S.C. 154(b) by 0 days.

(21) Appl. No.: 11/037,629

(22) Filed: Jan. 12, 2005

(65) Prior Publication Data

US 2005/0154468 A1 Jul. 14, 2005

Related U.S. Application Data

(60) Provisional application No. 60/535,741, filed on Jan. 13, 2004.

(51) Int. Cl.
*A61F 2/44* (2006.01)
(52) U.S. Cl. .................. 623/17.13; 623/17.14; 623/17.15; 623/17.16
(58) Field of Classification Search ............. 623/17.13, 623/17.14, 17.11, 17.12, 17.15, 17.16
See application file for complete search history.

(56) References Cited

U.S. PATENT DOCUMENTS

| 6,645,248 | B2* | 11/2003 | Casutt ..................... 623/17.12 |
| 7,048,764 | B2* | 5/2006 | Ferree ..................... 623/17.15 |
| 2003/0074068 | A1* | 4/2003 | Errico et al. ............. 623/17.14 |
| 2004/0133278 | A1* | 7/2004 | Marino et al. ........... 623/17.14 |
| 2004/0243240 | A1* | 12/2004 | Beaurain et al. ......... 623/17.14 |

OTHER PUBLICATIONS

The Random House College Dictionary, copyright 1980, the unabridged edition, p. 760.*

* cited by examiner

*Primary Examiner*—Corrine McDermott
*Assistant Examiner*—Thomas J. Sweet

(57) ABSTRACT

The instant invention proposes an artificial intervertebral disc providing for angular displacements between adjacent vertebrae wherein these displacements are accommodated by internal shear in an elastomeric layered element residing between the upper and lower bases attached, respectively, to the upper and lower adjacent vertebrae, without sliding.

3 Claims, 2 Drawing Sheets

ARTIFICIAL INTERVERTEBRAL DISC

Priority as of Jan. 13, 2004 is requested per Provisional Application 60/535,741.

FIELD OF THE INVENTION

The invention relates to designs of artificial intervertebral discs for prosthetic and dummy applications.

BACKGROUND OF THE INVENTION

Intervertebral disc prosthetics must comply with several requirements, often contradicting each other. These requirements are derived from studies on natural intervertebral discs. The prosthetic artificial disc should provide angular mobilities with specified ranges and stiffness values (two bending mobilities, fore-and-aft and side-to-side, and torsional around the axis of the spine), while accommodating large and varying axial (vertical) loading; it is desirable that the stiffness values are not significantly influenced by the changing vertical loads. Dummies are mock-ups of human bodies designed to simulate behavior of human bodies in extreme circumstances, e.g. crash dummies. Dummies are not, usually, equipped with all individual vertebras simulating the human spinal column but have structural elements rather crudely simulating the human spine. These structural elements will also be called "vertebras" in this Specification. Maintaining the structural characteristics of artificial intervertebral discs in close similarity to the natural discs is very important in order to adequately simulate behavior of the human bodies in the course of the dummy-based experiments.

There are various proposed designs of artificial intervertebral discs attempting to simulate structural characteristics, especially stiffness values and ranges of motion of the natural discs. The most widely used designs comprise spherical joints generated by a concave spherical socket engaged with a fitting convex spherical protrusion. Both surfaces are usually made from a low friction plastic capable of sliding without lubrication. While providing mobility in various angular directions and capable of accommodating axial loads, these designs have several shortcomings.

These artificial discs do not have elastic characteristics resident in the discs of the natural spinal column in any of the three angular directions. The natural elastic resistances to the motions approximately proportional to the deformation angle are replaced in these prosthetic or artificial discs by frictional resistances, practically independent on the motion magnitude.

Secondly, the motion resistances in all three directions (the friction forces) are increasing with the increasing axial force in the spinal column (which varies in the wide range). This also results in some unnatural feelings, since the elastic resistance forces in the natural spinal column are not significantly dependent on the axial force.

Another shortcoming of the state-of-the-art prosthetics is an unavoidable difference between static and dynamic friction coefficients in spherical joint. This makes the motion resistance different in the beginning of the movement and in the process of movement, since the static friction coefficient is greater than the dynamic friction coefficient.

Yet another shortcoming, which is also a result of frictional interaction in the spherical joint, is inevitable wear of the sliding connection. The wear is enhanced by sometimes high axial pressures in the spinal column which are too high for sliding plastic contacts. The wear process creates worn-out particles which are contaminating the area around the disc and may increase the friction forces if accumulated in the sliding connection.

The subject invention eliminates the listed shortcomings.

SUMMARY OF THE INVENTION

The instant invention proposes an artificial intervertebral disc providing for angular displacements between adjacent vertebrae wherein these displacements are accommodated by internal shear in an elastomeric layered element residing between the upper and lower adjacent vertebrae, without sliding.

The preferred embodiment of the invention has upper and lower rigid bases attached, respectively, to the upper and lower adjacent vertebrae. One of the bases has a spherical convex protrusion and another has a coaxial concave spherical socket, with these two spherical surfaces having the common center. The elastomeric layered element is placed between and attached to these convex and concave spherical surfaces.

In another embodiment of the proposed artificial intervertebral disc, both upper and lower bases have concave spherical sockets and an intermediate rigid element has two coaxial convex spherical protrusions on its upper and lower sides, with the upper protrusion being coaxial with and having the common center with the concave spherical socket on the upper base, with the lower protrusion being coaxial with and having the common center with the convex spherical socket on the lower base, and the elastomeric layered element consists of two elastomeric layers, one of which is placed between and attached to the two upper spherical surfaces and another is placed between and attached to the two lower spherical surfaces.

In another embodiment of the proposed artificial intervertebral disc, both upper and lower bases have convex spherical protrusions and an intermediate rigid element has two coaxial concave spherical sockets on its upper and lower sides, with the upper socket being coaxial with and having the common center with the convex spherical protrusion on the upper base, with the lower socket being coaxial with and having the common center with the convex spherical protrusion on the lower base, and the elastomeric layered element consists of two elastomeric layers, one of which is placed between and attached to the two upper spherical surfaces and another is placed between and attached to the two lower spherical surfaces.

Yet another embodiment of the proposed artificial intervertebral disc is characterized by having means for preloading the elastomeric layered element in compression.

DETAILED DESCRIPTION OF THE PREFERRED EMBODIMENTS

Figure 1:
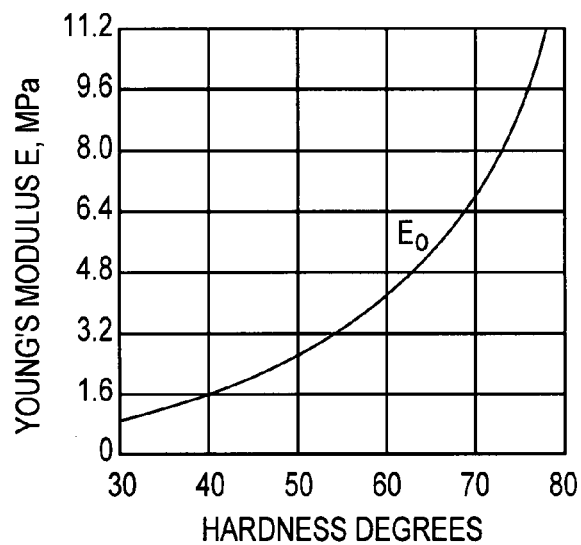
FIG. 1 shows a correlation between elastomer (rubber) hardness measured by standard measuring tool—Shore Durometer at its "A" scale and Young's modulus of the elastomer.

A "rigid" component in this Specification means a component having significantly lesser deformations than the elastomeric element(s) connecting these components. Specifically, "rigid" is defined here as having the Young's modulus at least ten times greater than the Young's modulus $E_0$ of an elastomer having hardness H60 on scale A of Shore Durometer. This corresponds, in accordance with the industry-accepted correlation shown in FIG. 1, to the Young's modulus $E \approx 3G \geq 10E_0 = \sim 40$ MPa, where G is the shear modulus.

Four embodiments of the proposed disc design are shown in FIGS. 2, 6, 7, and 8.

Figure 2:
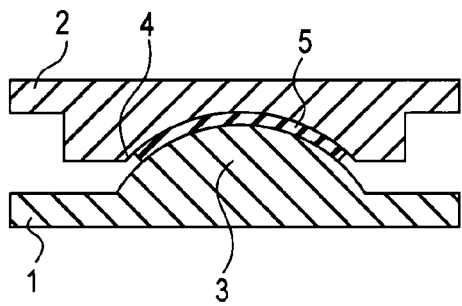
FIG. 2 shows a cross section of the proposed artificial intervertebral disc with elastomeric layered element placed between the spherical socket in the upper base and the spherical protrusion in the lower base.
Figure 3:
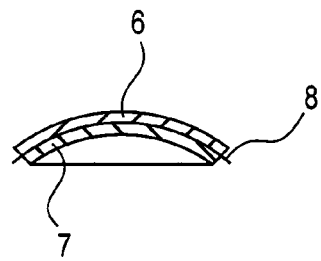
FIG. 3 gives a cross section of spherical elastomeric element constructed as a laminate with two layers of rubber and one intermediate layer of a rigid material.
Figure 4:
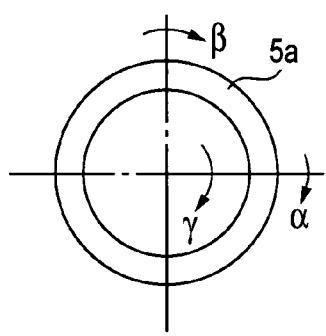
FIG. 4 shows a plan view of the elastomeric element shaped for providing a relatively high angular stiffness of the artificial disc around the spinal axis as compared with its bending angular stiffness values.
Figure 5:
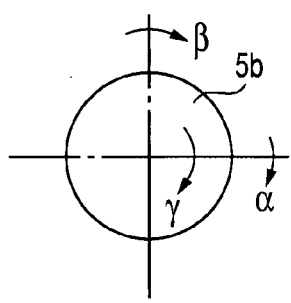
FIG. 5 shows a plan view of the elastomeric element shaped for providing a relatively low angular stiffness of the artificial disc around the spinal axis as compared with its angular bending stiffness values.

FIG. 2 shows an artificial disc comprising lower base 1 and upper base 2, both made of a metal, plastic, or other rigid material. One of the bases has a convex spherical protrusion 3 (shown on the lower base 1), while another base (top base 2 in FIG. 2) has a concave spherical socket 4 coaxial with protrusion 3. Bases 1 and 2 do not have a direct contact, and the space between protrusion 3 and socket 4 is filled with elastomeric element 5 which constitutes a layer or a laminate (see below) of uniform thickness, attached by known means (bonded, glued, mechanically attached, etc.) to both convex and concave spherical surfaces of protrusion 3 and socket 4. Elastomeric element 5 is shown in FIG. 2 as a "solid" rubber layer, contacting with the full surface area of socket 4 and protrusion 3. However, it can be designed with smaller area, as shown in FIGS. 4, 5 below. While an elastomeric element comprising one layer of rubber is shown in FIG. 2, it can be embodied as a rubber-metal laminate. Such a laminate comprising two layers 6 and 7 of rubber with thin layer 8 made of metal or other material rigid in extension, such as strong fabric, between the layers of rubber is shown in FIG. 3.

Bases 1 and 2 in FIG. 2 are attached, respectively, to the lower and upper adjacent vertebrae (not shown). It is preferable that the centers of both convex and concave spherical surfaces coincide at one point, thus minimizing the resistance forces for angular displacements between the connected vertebras. Spherical elastomeric layer or laminate 5 is conforming spherical surfaces of protrusion 3 and socket 4, and can have a shape providing for desirable stiffness values in different directions. For example, layers 5a and 5b of the same spherical radius shown in FIGS. 4 and 5, respectively, in the plan views are shown to have the same surface area, but different shapes, annular in FIG. 4 and solid of a small diameter in FIG. 5. As a result, they have the same angular (shear) stiffness in two bending directions shown as α and β, but layer 5a, FIG. 4, has significantly higher stiffness than layer 5b, FIG. 5, in γ direction (torsional stiffness, rotation about the spine axis). Other shapes of elastomeric element 5 in FIG. 2 may be beneficial in special cases.

While the artificial intervertebral disc shown in FIG. 2 has the convex spherical protrusion on the lower base and the concave spherical socket on the upper base, this arrangement can be reversed and the socket can be part of the lower base, while the spherical protrusion is made on the upper base.

If the artificial disc is intended to be used as a prosthetic device, then bases 1 and 2 as well as elastomeric element 5 must be made of bio-compatible materials.

In operation, an angular bending displacement between the adjacent vertebras in α and/or β directions would induce the same angular displacement between lower 1 and upper 2 bases attached to these vertebras. The relative angular displacement in α and/or β directions between bases 1 and 2 having, respectively, convex and concave spherical surfaces centered at the same point and separated by elastomeric layered element 5, will be accommodated by a shear deformation of element 5. The shear resistance associated with this deformation will be of an elastic nature characteristic for elastomeric (rubber-like) materials and is approximately proportional to magnitude of the shear deformation and to shear modulus $G=E_0/3$ of the elastomeric material. Axial forces in the spinal column cause compression deformation of the layered elastomeric element.

Numerous experiments have shown that the compression forces cause only a slight increase in the shear resistance, especially for thin layers of the elastomeric materials.

Since there is no direct sliding contact between the upper and lower bases, there is no friction and no wear in the proposed artificial disc system, which operates in a close similarity to the natural intervertebral disc.

Figure 6:
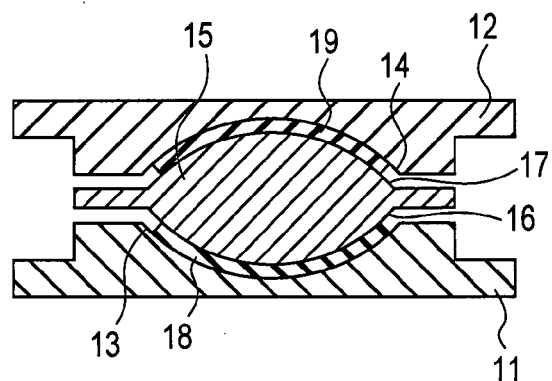
FIG. 6 depicts the axial cross section of the artificial spinal disc having an intermediate double-convex element interacting with the lower and upper bases via elastomeric layered element.

FIG. 6 illustrates another embodiment of the proposed prosthesis, comprising lower base 11 and top base 12 attached to the respective adjacent vertebrae. Each base has socket 13, 14, respectively, each socket having concave spherical surface. Intermediate element 15 has two convex spherical protrusions 16 and 17 with all four spherical surfaces being coaxial in the undeformed (initial) condition of the artificial disc. The elastomeric element comprises two elastomeric layers (shown) or laminates as presented in FIG. 3. The space between protrusion 16 and socket 13 is filled with elastomeric layer/laminate 18 of uniform thickness, attached (bonded, glued, etc.) to both convex and concave spherical surfaces of protrusion 16 and socket 13. The space between protrusion 17 and socket 14 is filled with a elastomeric layer/laminate 19 of uniform thickness, attached (bonded, glued, etc.) to both convex and concave spherical surfaces of protrusion 17 and socket 14.

Figure 7:
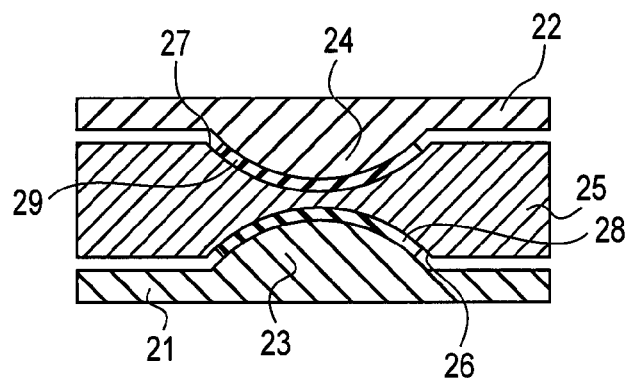
FIG. 7 depicts the axial cross section of the artificial spinal disc having an intermediate double-concave element interacting with the lower and upper bases via elastomeric layers.

FIG. 7 illustrates yet another embodiment of the proposed artificial intervertebral disc, comprising lower base 21 and top base 22 attached to the respective adjacent vertebrae. Each base has spherical protrusion 23, 24, respectively, each protrusion having convex spherical surface. Intermediate element 25 has two concave spherical sockets 26 and 27 with all four spherical surfaces being coaxial in the undeformed (initial) condition. The elastomeric element comprises two elastomeric layers (shown) or laminates as presented in FIG. 3. The space between socket 26 and protrusion 23 is filled with elastomeric layer/laminate 28 of uniform thickness, attached (bonded, glued, etc.) to both concave and convex spherical surfaces of socket 26 and protrusion 23. The space between socket 27 and protrusion 24 is filled with a elastomeric layer/laminate 29 of uniform thickness, attached (bonded, glued, etc.) to both concave and convex spherical surfaces of socket 27 and protrusion 24.

Figure 8:
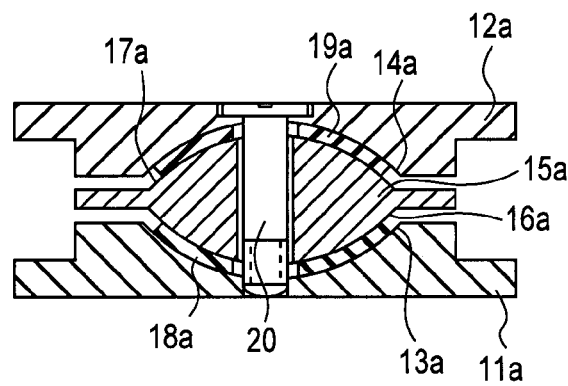
FIG. 8 illustrates modification of artificial discs with intermediate elements, as shown in FIGS. 6 and 7, which can be axially preloaded before insertion.

FIG. 8 shows an embodiment of the proposed prosthesis similar to the embodiment shown in FIG. 6 wherein the spherical joint is preloaded (and held captive) by means of preloading member 20 (a bolt is shown but other known designs of preloading elements can be employed). The preloading element 20 is attached to lower base 11a and top base 12a, but does not have a contact with intermediate element 15a. The artificial disc can be preloaded with a specified load before insertion into the spinal column, resulting in modification of the axial stiffness.

A similar preloading system can be applied to the embodiment shown in FIG. 7.

It is readily apparent that the components of the artificial intervertebral disc disclosed herein may take a variety of configurations. Thus, the embodiments and exemplifications shown and described herein are meant for illustrative purposes only and are not intended to limit the scope of the present invention, the true scope of which is limited solely by the claims appended thereto.

The invention claimed is:

1. An artificial intervertebral disc, comprising:
lower and upper bases, each made from a rigid material and each adapted to attach, respectively, to the lower and upper adjacent vertebras;
said lower and upper bases having relative mobilities in three angular coordinate directions;
wherein one of said rigid lower and upper bases has a convex spherical protrusion and the other of said lower and upper bases has a concave spherical socket co-axial with said convex spherical protrusion, with an elastomeric layered element of a uniform thickness residing between, conforming with, and adapted to attach to said spherical surfaces of said protrusion and said socket on said lower and upper bases, with the coinciding center points of said convex spherical protrusion and concave spherical socket,
with all these relative mobilities resulting from shear deformations within said elastomeric layered element of a uniform thickness attached to said spherical surfaces.

2. The artificial intervertebral disc of claim 1, wherein said elastomeric layered elements comprise one uniform thickness layer of an elastomeric material.

3. The artificial intervertebral disc of claim 1 wherein said elastomeric layered element attached to said spherical surfaces has an annular shape thus allowing independent modification of shear stiffness values independently for various angular coordinate directions.

* * * * *